United States Patent
Tose et al.

(10) Patent No.: US 11,753,391 B2
(45) Date of Patent: Sep. 12, 2023

(54) METHOD FOR PRODUCING GLYCOLIDE

(71) Applicant: Kureha Corporation, Tokyo (JP)

(72) Inventors: Takenori Tose, Tokyo (JP); Yoshinori Suzuki, Tokyo (JP); Yuta Yamadoi, Tokyo (JP)

(73) Assignee: Kureha Corporation, Tokyo (JP)

( * ) Notice: Subject to any disclaimer, the term of this patent is extended or adjusted under 35 U.S.C. 154(b) by 15 days.

(21) Appl. No.: 16/980,626

(22) PCT Filed: Feb. 14, 2019

(86) PCT No.: PCT/JP2019/005348
§ 371 (c)(1),
(2) Date: Sep. 14, 2020

(87) PCT Pub. No.: WO2019/181298
PCT Pub. Date: Sep. 26, 2019

(65) Prior Publication Data
US 2021/0017146 A1 Jan. 21, 2021

(30) Foreign Application Priority Data
Mar. 20, 2018 (JP) .................. 2018-052285

(51) Int. Cl.
*C07D 319/12* (2006.01)
(52) U.S. Cl.
CPC .................. *C07D 319/12* (2013.01)
(58) Field of Classification Search
CPC .............. C07D 319/12; C07B 61/00
See application file for complete search history.

(56) References Cited

U.S. PATENT DOCUMENTS

| | | | | |
|---|---|---|---|---|
| 6,891,048 B2 * | 5/2005 | Yamane | ............... | C07D 319/12 549/274 |
| 2004/0087805 A1 | 5/2004 | Yamane et al. | | |
| 2016/0002196 A1 | 1/2016 | Ikeyama et al. | | |

FOREIGN PATENT DOCUMENTS

| | | |
|---|---|---|
| CN | 1496359 A | 5/2004 |
| CN | 101054371 A | 10/2007 |
| CN | 104903306 A | 9/2015 |
| FI | 980839 A | 10/1999 |
| JP | H8-119961 A | 5/1996 |
| JP | 2004-519485 A | 7/2004 |
| JP | 2006-104138 A | 4/2006 |
| WO | WO 02/070508 A2 | 9/2002 |

OTHER PUBLICATIONS

CN 101054371A by Yang, Publication Date Oct. 17, 2007—English machine translation by Espacenet.*
Extended European Search Report dated Mar. 5, 2021, in European Patent Application No. 19770880.3.
International Search Report of the International Searching Authority for PCT/JP2019/005348 dated May 14, 2019.
English translation of International Search Report of the International Searching Authority for PCT/JP2019/005348 dated May 14, 2019.
English translation of International Preliminary Report on Patentability and Written Opniion dated Sep. 22, 2020, in PCT/JP2019/005348.
Chinese Office Action and Search Report for Chinese Application No. 201980014073.7, dated Sep. 15, 2022, with an English translation.
Chinese Office Action for corresponding Chinese Application No. 201980014073.7, dated Mar. 14, 2023, with English translation.

* cited by examiner

*Primary Examiner* — Valerie Rodriguez-Garcia
(74) *Attorney, Agent, or Firm* — Birch, Stewart, Kolasch & Birch, LLP

(57) ABSTRACT

The object of the present invention is to provide a method for producing glycolide, with which a production rate of glycolide can be further enhanced.
The method for producing glycolide that achieves the object described above includes: an oligomer preparation step of heating an aqueous glycolic acid solution and subjecting glycolic acid contained in the aqueous glycolic acid solution to dehydrating polycondensation, to obtain a glycolic acid oligomer; and a depolymerization step of depolymerizing the glycolic acid oligomer in the presence of ferrous ions to obtain glycolide.

6 Claims, No Drawings

METHOD FOR PRODUCING GLYCOLIDE

TECHNICAL FIELD

The present invention relates to a method for producing glycolide.

BACKGROUND ART

Polyglycolic acid is a resin material having, for example, excellent biodegradability, gas barrier properties, and strength and has been used in a wide variety of technical fields such as resin materials for various industrial products, such as polymer materials for medical purposes such as sutures and artificial skins, packaging materials such as bottles and films, injection molded products, fibers, deposited films, and fishing lines.

Depending on use, such a polyglycolic acid is required to have a high degree of polymerization. A polyglycolic acid having a high degree of polymerization can be produced by a method in which glycolide is subjected to ring-opening polymerization. Furthermore, reduction of production cost of polyglycolic acid has been demanded, and realization of mass production of glycolide, which is a raw material, that is, production of glycolide at a high production rate, has been demanded.

Glycolide, which serves as a raw material of polyglycolic acid, is produced by 1) producing a glycolic acid oligomer by subjecting glycolic acid to dehydrating polycondensation (dehydrating polycondensation) and 2) depolymerizing the obtained glycolic acid oligomer (depolymerization).

Note that if alkali metal ions are present in the reaction system of the depolymerization of step 2) described above, depolymerization reaction becomes unstable, and the glycolide tends to be colored. Therefore, it has been proposed that the depolymerization of step 2) is performed in the presence of a stabilizer, such as ferric sulfate (e.g. Patent Document 1).

CITATION LIST

Patent Document

Patent Document 1: JP 2004-519485 T

SUMMARY OF INVENTION

Technical Problem

In the method for producing glycolide described in Patent Document 1, since the alkali metal ions are trapped by the stabilizer, less colored glycolide can be produced. However, from the perspective of further reducing production cost of a polyglycolic acid having a high degree of polymerization, further enhancement of production rate of glycolide, which serves as a raw material, has been demanded.

The present invention was completed in the light of such circumstances and aims to provide a method for producing glycolide, with which a production rate of the glycolide can be further enhanced.

Solution to Problem

The method for producing glycolide according to an embodiment of the present invention includes: an oligomer preparation step of heating an aqueous glycolic acid solution and subjecting glycolic acid contained in the aqueous glycolic acid solution to dehydrating polycondensation, to obtain a glycolic acid oligomer; and a depolymerization step of depolymerizing the glycolic acid oligomer in the presence of ferrous ions to obtain glycolide.

Advantageous Effects of Invention

According to the present invention, a method for producing glycolide, with which a production rate of the glycolide can be further enhanced, can be provided.

DESCRIPTION OF EMBODIMENTS

1. Method for Producing Glycolide

The method for producing glycolide according to an embodiment of the present invention includes: an oligomer preparation step of heating an aqueous glycolic acid solution and subjecting glycolic acid to dehydrating polycondensation, to obtain a glycolic acid oligomer; and a depolymerization step of depolymerizing the obtained glycolic acid oligomer in the presence of ferrous ions to obtain glycolide.

In the related art, for example, use of ferric sulfate as a stabilizer (trapping agent for alkali metal ions) during depolymerization has been proposed. However, although coloration of glycolide can be suppressed by the ferric sulfate, it was difficult to dramatically increase the production rate of glycolide. In contrast, the present inventors found that the production rate of glycolide is dramatically increased by using ferrous ions as a catalyst during depolymerization.

Note that there are two methods for using ferrous ions as a catalyst in the depolymerization of a glycolic acid oligomer, and the methods are (1) a method of adding a salt of ferrous iron to a reaction system (hereinafter, also referred to as "first method for producing glycolide") and (2) a method of adding a salt of ferric iron and a reducing agent therefor to a reaction system (hereinafter, also referred to as "second method for producing glycolide"). Therefore, these methods are separately described below.

(1) First Method for Producing Glycolide

The first method for producing glycolide can be a method including a) a ferrous salt addition step of adding a salt of ferrous iron to an aqueous glycolic acid solution, b) an oligomer preparation step of heating the aqueous glycolic acid solution and subjecting glycolic acid contained in the aqueous glycolic acid solution to dehydrating polycondensation, to obtain a glycolic acid oligomer, and c) a depolymerization step of depolymerizing the glycolic acid oligomer to obtain glycolide. However, as long as the objective and effect of the present invention are not impaired, another step may be included. Each of the steps will be explained below.

a) Ferrous Salt Addition Step

The ferrous salt addition step is a step of adding a salt of ferrous iron (hereinafter, also referred to as "ferrous salt") to an aqueous glycolic acid solution. The timing of performing the ferrous salt addition step is not particularly limited as long as the ferrous salt addition step is performed before the c) depolymerization step described below. The ferrous salt addition step may be performed before the b) oligomer preparation step described below or may be performed concurrently with the b) oligomer preparation step. Furthermore, the ferrous salt addition step may be performed only once or may be performed twice or more.

Note that it is conceived that a catalyst for enhancing the production rate of glycolide (ferrous ions) is typically added in the c) depolymerization step. However, the c) depolymerization step is typically performed in an organic solvent.

Furthermore, it is difficult to dissolve the ferrous salt in an organic solvent, and ferrous ions are less likely to be formed in the organic solvent. Therefore, by adding ferrous salt and ionizing it in an aqueous glycolic acid solution to prepare glycolic acid oligomer, the ferrous ions can adequately function as a catalyst in the c) depolymerization step.

Furthermore, by adding the ferrous salt to the aqueous glycolic acid solution, the production rate of glycolide is dramatically increased. The reason for this can be conceived as follows. When a ferrous salt is added to the aqueous glycolic acid solution, ferrous ions are suitably dispersed in a glycolic acid oligomer prepared in the b) oligomer preparation step. Furthermore, in this case, even in the c) depolymerization step, the condition in which ferrous ions are suitably dispersed in the glycolic acid oligomer is maintained, and the ferrous ions adequately function as a catalyst.

Also in the b) oligomer preparation step, it is conceived that the ferrous ions function as a catalyst for dehydrating polycondensation of glycolic acid. Therefore, it is conceived that, as a result of the ferrous ions suitably functioning as a catalyst both in b) oligomer preparation step and c) depolymerization step, the production rate of glycolide is dramatically enhanced.

In this step, the ferrous salt added in the aqueous glycolic acid solution is not particularly limited as long as the ferrous salt can be dissolved in water and form ferrous ions, and examples thereof include inorganic acid salts, organic acid salts, and complex salts. Examples of the inorganic acid salt include ferrous sulfate, ferrous chloride, ferrous nitrate, ferrous nitrite, ferrous sulfite, and ferrous cyanide. Examples of the organic acid salt include salts of aliphatic carboxylic acids and ferrous iron and salts of aromatic carboxylic acids and ferrous iron. Examples of the aliphatic carboxylic acid include formic acid, acetic acid, oxalic acid, malonic acid, succinic acid, glutaric acid, lactic acid, glycolic acid, butanoic acid, pentanoic acid, hexanoic acid, heptanoic acid, octanoic acid, dodecanoic acid, stearic acid, and oleic acid. Furthermore, examples of the aromatic carboxylic acid include phthalic acid, benzoic acid, and salicylic acid. Furthermore, examples of a ligand of the complex salt include ligands having an acyl group or a nitrile group. For the ferrous salt added in the ferrous salt addition step, only a single type may be used, or two or more types may be used. As the ferrous salt, inorganic acid salts are preferred from the perspective of stability in the aqueous solution, and among these, ferrous sulfate and ferrous chloride are preferred from the perspectives of, for example, availability and cost. Furthermore, among the organic acid salts, a salt of glycolic acid, which is an organic acid originally contained in the aqueous glycolic acid solution, is preferable from the perspective of suppressing side reactions of the organic acid.

The form of the ferrous salt may be a form that can be charged into a reactor, and may be a powder or clump form. Among these, from the perspective of ease of uniform dispersion in the aqueous glycolic acid solution, a powder form is preferred. Furthermore, the ferrous salt may be dissolved in advance in a solvent (e.g. water) and then mixed in the aqueous glycolic acid solution.

The addition amount of the ferrous salt is not particularly limited, but is preferably an addition amount, at which the amount of the ferrous iron relative to the amount of the glycolic acid contained in the aqueous glycolic acid solution is preferably from 0.01 to 1000 ppm, more preferably from 0.1 to 100 ppm, and even more preferably from 1 to 10 ppm. Note that, in the case where the ferrous salt addition step is performed for a plurality of times, the total amount of the ferrous salt added to the aqueous glycolic acid solution is preferably in the range described above. When the addition amount of the ferrous salt is greater than or equal to a certain amount, the rates of dehydrating polycondensation reaction of the glycolic acid and the depolymerization reaction of the glycolic acid oligomer tend to be adequately enhanced, and the production rate of glycolide is thus enhanced. On the other hand, when the addition amount of the ferrous salt is less than or equal to a certain amount, an amount of undissolved ferrous salt is decreased.

Note that, in a case where ferrous ions can be supplied in the c) depolymerization step by another method, the a) ferrous salt addition step is not necessary. Examples of another method include a method of adding a ferrous salt to the glycolic acid oligomer. As such a ferrous salt, a ferrous salt that releases the ligand in the glycolic acid oligomer is preferred and, specifically, carboxylate of ferrous iron is preferred.

Meanwhile, the aqueous glycolic acid solution, to which the ferrous salt is added, is a solution containing glycolic acid and water. The aqueous glycolic acid solution may contain another component other than the glycolic acid and water as long as the objective and effect of the present invention are not impaired.

The aqueous glycolic acid solution can be prepared by dissolving glycolic acid, a glycolic acid ester (e.g., lower alkyl ester), or a glycolic acid salt (e.g., sodium salt) in water.

The amount of the glycolic acid in the aqueous glycolic acid solution can be, for example, from 1 mass % to 99 mass %.

Furthermore, from the perspective of obtaining high purity glycolide, as the aqueous glycolic acid solution, use of an aqueous glycolic acid solution of high purity having a low content of impurity, such as organic materials and metal ions, is preferred.

From the perspective of uniformly dissolve the ferrous salt, addition of the ferrous salt to the aqueous glycolic acid solution may be performed while the aqueous glycolic acid solution is heated. Furthermore, from the similar perspective, addition of the ferrous salt may be performed while the aqueous glycolic acid solution is agitated.

b) Oligomer Preparation Step

In the oligomer preparation step, a glycolic acid oligomer is obtained by heating the aqueous glycolic acid solution described above and subjecting the glycolic acid contained in the aqueous glycolic acid solution to dehydrating polycondensation. Specifically, the aqueous glycolic acid solution is heated to polycondense the glycolic acid until distillation of low molecular weight substances, such as water and alcohol, substantially stops.

The dehydrating polycondensation of the glycolic acid may be performed in the presence of a condensation catalyst or a transesterification catalyst, as necessary. Furthermore, the dehydrating condensation may be performed in any atmosphere of a normal pressure atmosphere, a reduced pressure atmosphere, or a pressurized atmosphere.

Furthermore, the heating temperature (dehydrating polycondensation temperature) during the dehydrating polycondensation reaction is preferably from 50° C. to 300° C., more preferably from 100° C. to 250° C., and even more preferably from 140° C. to 230° C.

After completion of the dehydrating polycondensation reaction, the formed glycolic acid oligomer may be used as is as a raw material for the depolymerization step described below.

The weight average molecular weight (Mw) of the glycolic acid oligomer prepared in the present step is preferably from 1000 to 100000, and more preferably from 10000 to 100000, from the perspective of yield of glycolide. The weight average molecular weight (Mw) can be measured by gel permeation chromatography (GPC).

From the perspective of yield of glycolide during the depolymerization reaction, the melting point (Tm) of the obtained glycolic acid oligomer is, for example, preferably 140° C. or higher, more preferably 160° C. or higher, and even more preferably 180° C. or higher. The upper limit of the melting point (Tm) of the glycolic acid oligomer is, for example, 220° C. The melting point (Tm) of the glycolic acid oligomer can be measured by an endothermic peak temperature when the temperature is increased at a rate of 10° C./min in an inert gas atmosphere, by using a differential scanning calorimeter (DSC).

c) Depolymerization Step

In the depolymerization step, the glycolic acid oligomer obtained in the b) oligomer preparation step described above is heated and depolymerized, and thus glycolide is obtained. Specifically, the glycolic acid oligomer is depolymerized in an organic solvent to obtain glycolide.

In the depolymerization step, first, the glycolic acid oligomer is added to an organic solvent described below and heated under normal pressure or reduced pressure to dissolve the glycolic acid oligomer in the organic solvent.

From the perspectives of increasing adequately the depolymerization reaction temperature and facilitating enhancement of the production rate of glycolide, the organic solvent is preferably an organic solvent having a high boiling point of 230° C. to 450° C. The boiling point of the organic solvent is more preferably 235° C. to 450° C., even more preferably 255° C. to 430° C., and particularly preferably 280° C. to 420° C.

Examples of the organic solvent having the boiling point described above include aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters, and aromatic phosphoric acid esters. Among these, aromatic dicarboxylic acid diesters, aromatic carboxylic acid esters, aliphatic dicarboxylic acid diesters, and polyalkylene glycol diethers are preferred. For example, from the perspective of being less likely to cause thermal degradation, a polyalkylene glycol diether is more preferred.

As the polyalkylene glycol diether, a polyalkylene glycol diether represented by Formula (1) below is preferred.

[Chemical Formula 1]

X—O—(—R—O—)p-Y    (1)

In Formula (1), R represents a methylene group or a linear or branched alkylene group having from 2 to 8 carbons. X and Y each represent an alkyl group having from 2 to 20 carbons or an aryl group. p represents an integer from 1 to 5. When p is 2 or greater, a plurality of R moieties may be the same or different.

Examples of the polyalkylene glycol diether include polyalkylene glycol dialkyl ether, polyalkylene glycol alkylaryl ether, and polyalkylene glycol diaryl ether.

Examples of the polyalkylene glycol dialkyl ether include diethylene glycol dialkyl ethers, such as diethylene glycol dibutyl ether, diethylene glycol dihexyl ether, diethylene glycol dioctyl ether, diethylene glycol butyl-2-chlorophenyl ether, diethylene glycol butylhexyl ether, diethylene glycol butyloctyl ether, and diethylene glycol hexyloctyl ether; triethylene glycol dialkyl ethers, such as triethylene glycol diethyl ether, triethylene glycol dipropyl ether, triethylene glycol dibutyl ether, triethylene glycol dihexyl ether, triethylene glycol dioctyl ether, triethylene glycol butyloctyl ether, triethylene glycol butyldecyl ether, triethylene glycol butylhexyl ether, and triethylene glycol hexyloctyl ether; tetraethylene glycol dialkyl ethers, such as polyethylene glycol dialkyl ethers such as tetraethylene glycol diethyl ether, tetraethylene glycol dipropyl ether, tetraethylene glycol dibutyl ether, tetraethylene glycol dihexyl ether, tetraethylene glycol dioctyl ether, tetraethylene glycol butylhexyl ether, tetraethylene glycol butyloctyl ether, and tetraethylene glycol hexyloctyl ether; polypropylene glycol dialkyl ether in which an ethyleneoxy group in the polyalkylene glycol dialkyl ethers is substituted with a propyleneoxy group, and polybutylene glycol dialkyl ether in which an ethyleneoxy group in the polyalkylene glycol dialkyl ethers is substituted with a butyleneoxy group.

Examples of the polyalkylene glycol alkylaryl ether include diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether, tetraethylene glycol octylphenyl ether, and polyethylene glycol alkylaryl ether in which some of hydrogen atoms of the phenyl group in these compounds are substituted with alkyl, alkoxy, or halogen atom(s); polypropylene glycol alkylaryl ether in which an ethyleneoxy group in the polyalkylene glycol alkylaryl ethers is substituted with a propyleneoxy group, and polybutylene glycol alkylaryl ether in which an ethyleneoxy group in the polyalkylene glycol alkylaryl ethers is substituted with a butyleneoxy group.

Examples of the polyalkylene glycol diaryl ether include diethylene glycol diphenyl ether, triethylene glycol diphenyl ether, tetraethylene glycol diphenyl ether, and polyethylene glycol diaryl ether in which some hydrogen atoms of the phenyl group in these compounds are substituted with alkyl, alkoxy, or halogen atom(s); polypropylene glycol diaryl ether in which an ethyleneoxy group in the polyalkylene glycol diaryl ether is substituted with a propyleneoxy group, and polybutylene glycol diaryl ether in which an ethyleneoxy group in the polyalkylene glycol diaryl ether is substituted with a butyleneoxy group.

Among these, from the perspective of being less likely to cause thermal degradation or the like, polyalkylene glycol dialkyl ethers are preferred, and tetraethylene glycol dibutyl ether, triethylene glycol butyloctyl ether, diethylene glycol dibutyl ether, and diethylene glycol butyl-2-chlorophenyl ether are more preferred, and from the perspective of recovery rate of glycolide or the like, tetraethylene glycol dibutyl ether and triethylene glycol butyloctyl ether are even more preferred.

The amount of the organic solvent is, for example, preferably from 30 to 5000 parts by mass, more preferably from 50 to 2000 parts by mass, and even more preferably from 100 to 1000 parts by mass, per 100 parts by mass of the glycolic acid oligomer.

Furthermore, to enhance solubility of the glycolic acid oligomer in the organic solvent, as necessary, a solubilizing agent may be further added to the reaction system.

The solubilizing agent can be a non-basic organic compound having a boiling point of 180° C. or higher, such as monohydric alcohols, polyhydric alcohols, phenols, monovalent aliphatic carboxylic acids, polyvalent aliphatic carboxylic acids, aliphatic amides, aliphatic imides, and sulfonic acids. Among these, from the perspective of ease in achieving effect of a solubilizing agent, monohydric alcohols and polyhydric alcohols are preferred.

The boiling point of the monohydric or polyhydric alcohol is preferably 200° C. or higher, more preferably 230° C. or higher, and particularly preferably 250° C. or higher.

The monohydric alcohols are particularly preferably polyalkylene glycol monoether represented by Formula (2) below.

[Chemical Formula 2]

$$HO-(R^1-O)q-X^1 \qquad (2)$$

In Formula (2), $R^1$ represents a methylene group or a linear or branched alkylene group having from 2 to 8 carbons. $X^1$ represents a hydrocarbon group. The hydrocarbon group is preferably an alkyl group. q represents an integer of 1 or greater. When q is 2 or greater, a plurality of $R^1$ moieties may be the same or different.

Examples of the polyalkylene glycol monoethers include polyethylene glycol monoethers, such as polyethylene glycol monomethyl ether, polyethylene glycol monoethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; polypropylene glycol monoethers in which an ethyleneoxy group in the polyethylene glycol monoethers is substituted with a propyleneoxy group; and polybutylene glycol monoether in which an ethyleneoxy group in the polyethylene glycol monoethers is substituted with a butyleneoxy group. Among these, a polyalkylene glycol monoether, in which the alkyl group contained in the ether group has from 1 to 18 carbons, and preferably from 6 to 18 carbons, is preferred, and a polyethylene glycol monoalkyl ether, such as triethylene glycol monooctyl ether, is more preferred.

When the polyalkylene glycol monoether is added, solubility of glycolic acid oligomer is enhanced. Therefore, by using the polyalkylene glycol monoether as a solubilizing agent, depolymerization reaction of the glycolic acid oligomer tends to be progress more rapidly.

The polyhydric alcohols are particularly preferably polyalkylene glycol represented by Formula (3) below.

[Chemical Formula 3]

$$HO-(R^2-O)r-H \qquad (3)$$

In Formula (3), $R^2$ represents a methylene group or a linear or branched alkylene group having from 2 to 8 carbons. r represents an integer of 1 or greater. When r is 2 or greater, a plurality of $R^2$ moieties may be the same or different.

Examples of polyalkylene glycol include polyethylene glycol, polypropylene glycol, and polybutylene glycol.

The addition amount of the solubilizing agent is preferably from 0.1 to 500 parts by mass, and more preferably from 1 to 300 parts by mass, per 100 parts by mass of the glycolic acid oligomer. When the addition amount of the solubilizing agent is greater than or equal to a certain amount, solubility of the glycolic acid oligomer in the organic solvent tends to be adequately enhanced. By setting the addition amount of the solubilizing material to not greater than a certain amount, cost required to recover the solubilizing agent can be reduced.

Then, the solution described above is heated under normal pressure or reduced pressure to depolymerize the glycolic acid oligomer, and thus glycolide is obtained. At this time, in the production method according to an embodiment of the present invention, because ferrous ions function as a catalyst, the production rate of glycolide is remarkably enhanced.

The heating temperature (depolymerization temperature) during the depolymerization reaction has only to be not lower than the temperature that causes depolymerization of the glycolic acid oligomer and also depends on, for example, the degree of pressure reduction and type of high boiling point organic solvent. The heating temperature is typically 200° C. or higher, preferably from 200° C. to 350° C., more preferably 210° C. to 310° C., even more preferably 220° C. to 300° C., and yet even more preferably 230° C. to 290° C.

The heating during the depolymerization reaction may be performed under normal pressure or reduced pressure but is preferably performed under reduced pressure from 0.1 kPa to 90 kPa. Since a lower pressure results in lower depolymerization reaction temperature, the heating temperature is decreased easily, and thus high recovery rate of the solvent is achieved. The degree of pressure reduction is preferably from 1 kPa to 60 kPa, more preferably from 1.5 kPa to 40 kPa, and particularly preferably from 2 kPa to 30 kPa.

Note that, during the depolymerization reaction, the ferrous ions described above may be oxidized (e.g., becomes ferric ions) and deactivated. Therefore, as necessary, an activator may be added in the reaction system to activate such the deactivated ferrous ions. Note that the activator may be added after the ferrous ions is deactivated and may be added in the organic solvent together with glycolic acid oligomer and the like in advance. In the case where the activator is added in advance, oxidation of the ferrous ions can be inhibited by the activator for a long period of time, and thus deactivation of the ferrous ions can be suppressed.

Note that the oxidation-reduction potential from the ferrous ion to the ferric ion is 0.78 V. Therefore, examples of the activator include metals, metal compounds, or organic compounds, which have an oxidation-reduction potential of lower than 0.78 V. Specific examples of the activator include copper chloride (CuCl), Mn, and vitamin C. Among these, Mn exhibiting high effect of activation is preferred.

The addition amount (mole) of the activator is preferably from 0.1 to 20, more preferably from 1 to 10, and even more preferably from 2 to 5, when the amount (mole) of iron ions present in the reaction system is 1. When the amount of the activator relative to the amount of iron ions is greater than or equal to a certain amount, the deactivated ferrous ions (e.g., ferric ions) tends to be reduced, and the depolymerization reaction tends to be promoted. On the other hand, when the amount of the activator is less than or equal to a certain amount, for example, cost and operation for recovery operation of the activator are reduced.

Note that the depolymerization reaction can be performed in a continuous system or a batch system; however, from the perspective of productivity of glycolide, the depolymerization reaction is preferably performed in a continuous system. In the case where a continuous system is employed, formed glycolide is vaporized for recovery concurrently with the depolymerization reaction described above. Specifically, formed glycolide is co-distilled together with the organic solvent and removed out of the depolymerization reaction system. By distilling the formed glycolide and the organic solvent together, adherence and accumulation of the glycolide on the wall surface of the reactor or line can be prevented. The distillation of the glycolide from the reaction system may be performed continuously or intermittently.

The glycolide is then recovered from the obtained distillate. Specifically, the distillate is cooled and subjected to phase separation to allow the glycolide to be precipitated.

The precipitated glycolide was separated from the mother liquor by a method such as filtration, centrifugal separation, or decantation, and recovered.

The mother liquor from which the glycolide has been separated may be reused as is without purification or may be reused after filtered and purified by treatment with activated carbon or the like or after distilled again and purified.

Meanwhile, when the glycolide is distilled from the reaction system, the amount of the reaction solution in the depolymerization reaction system (e.g. amount of organic solvent and amount of glycolic acid oligomer to perform depolymerization reaction) decreases. Therefore, as necessary, the organic solvent and the glycolic acid oligomer may be added to the system. The addition of the organic solvent and the glycolic acid oligomer may be performed after the recovery of glycolide or may be performed concurrently with the recovery of glycolide. By adding the amounts of the glycolic acid oligomer and the organic solvent corresponding to the distilled amount into the depolymerization reaction system, the depolymerization reaction can be performed continuously for a long period of time.

(2) Second Method for Producing Glycolide

The second method for producing glycolide can be a method including d) a ferric salt addition step of adding a salt of ferric iron to an aqueous glycolic acid solution, e) a reducing agent addition step of adding a reducing agent to reduce ferric ions originated from the ferric salt to ferrous ions, f) an oligomer preparation step of heating an aqueous glycolic acid solution and subjecting glycolic acid contained in the aqueous glycolic acid solution to dehydrating polycondensation, to obtain a glycolic acid oligomer, and g) a depolymerization step of depolymerizing the glycolic acid oligomer to obtain glycolide. Note that the f) oligomer preparation step and the g) depolymerization step are the same as those for the first method for producing glycolide described above. Thus, the d) ferric salt addition step and the e) reducing agent addition step are described here.

d) Ferric Salt Addition Step

The ferric salt addition step is a step of adding a salt of ferric iron (hereinafter, also referred to as "ferric salt") to an aqueous glycolic acid solution. The timing of performing the ferric salt addition step is not particularly limited as long as the ferric salt addition step is performed before the g) depolymerization step. The ferric salt addition step may be performed before the f) oligomer preparation step or may be performed concurrently with the f) oligomer preparation step. Furthermore, the ferric salt addition step may be performed only once or may be performed twice or more.

As described above, it is conceived that a catalyst for enhancing the production rate of glycolide (ferrous ions) is typically added in the g) depolymerization step. However, the g) depolymerization step is typically performed in an organic solvent. Furthermore, it is difficult to dissolve the ferric salt in an organic solvent. Therefore, in the second method for producing glycolide, by adding ferric salt in an aqueous glycolic acid solution to prepare glycolic acid oligomer, the ferric ions are formed. Furthermore, by reducing the ferric ions by a reducing agent described below, the ferrous ions can be introduced in the reaction system of the g) depolymerization step, and it is possible for the ferrous ions to adequately function as a catalyst during the depolymerization.

By adding the ferric salt to the aqueous glycolic acid solution and, further, reducing the ferric iron to the ferrous iron, the production rate of glycolide can be enhanced. The reason for this can be conceived as follows. When a ferric salt is added to an aqueous glycolic acid solution, ferric ions (ferrous ions in the case where reduction is performed by the reducing agent described below) are suitably dispersed in a glycolic acid oligomer prepared in the f) oligomer preparation step. Furthermore, by suitably reducing the ferric ions to the ferrous ions, in the g) depolymerization step, the condition in which ferrous ions are suitably dispersed in the glycolic acid oligomer can be achieved, and the ferrous ions adequately function as catalysts.

In this step, the ferric salt added in the aqueous glycolic acid solution is not particularly limited as long as the ferric salt can be dissolved in water and form a ferric ion, and examples thereof include inorganic acid salts, organic salts, and complex salts. Examples of the inorganic acid salt include ferric sulfate, ferric chloride, ferric nitrate, ferric nitrite, ferric sulfite, and ferric cyanide. Examples of the organic acid salt include salts of aliphatic carboxylic acids and ferric iron and salts of aromatic carboxylic acids and ferric iron. The organic acid can be the same as the acid contained in the ferrous salt. Furthermore, the ligand of the complex salt can be the same as the ligand contained in the ferrous salt. These may be used alone as one type, or two or more types of these may be used in combination. As the ferric salt, inorganic acid salts are preferred from the perspective of stability in the aqueous solution, and among these, ferric chloride is particularly preferred from the perspectives of, for example, availability and cost. Furthermore, among the organic acid salts, a salt of glycolic acid, which is an organic acid originally contained in the aqueous glycolic acid solution, is preferable from the perspective of suppressing side reactions of the organic acid.

The form of the ferric salt may be a form that can be charged into a reactor, and may be a powder or clump form. Among these, from the perspective of ease of uniform dispersion in an aqueous glycolic acid solution, a powder form is preferred.

The addition amount of the ferric salt is not particularly limited, but is preferably an addition amount, at which the amount of the ferric iron relative to the amount of the glycolic acid contained in the aqueous glycolic acid solution is preferably from 0.01 to 1000 ppm, more preferably from 0.1 to 100 ppm, and even more preferably from 1 to 10 ppm. Note that, in the case where the ferric salt addition step is performed for a plurality of times, the total amount of the ferric salt added to the aqueous glycolic acid solution is preferably in the range described above. When the addition amount of the ferric salt is greater than or equal to a certain amount, the rate of dehydrating polycondensation reaction of the glycolic acid tends to be enhanced. Furthermore, the amount of the ferrous ions obtained by reducing the ferric ions can be adequate, and the rate of the depolymerization reaction of the glycolic acid oligomer tends to be increased. On the other hand, when the addition amount of the ferric salt is less than or equal to a certain amount, an amount of undissolved ferric salt is decreased.

Note that, if the ferric ions can be supplied by another method and reduction can be performed by a reducing agent added in the e) reducing agent addition step described below, the d) ferric salt addition step is not necessary. Examples of another method include a method of adding a ferric salt to a glycolic acid oligomer. As such a ferric salt, a ferric salt that releases the ligand in the glycolic acid oligomer is preferred and, specifically, carboxylate of ferric iron is preferred.

Meanwhile, the aqueous glycolic acid solution to which the ferric salt is added can be the same as the aqueous glycolic acid solution used in the first method for producing glycolide described above.

Note that, from the perspective of ease of uniform dissolution of the ferric salt, addition of the ferric salt to the aqueous glycolic acid solution may be performed while the aqueous glycolic acid solution is heated. Furthermore, from the similar perspective, addition of the ferric salt may be performed while the aqueous glycolic acid solution is agitated. Furthermore, the ferric salt may be dissolved in advance in a solvent (e.g., water) and then mixed in the aqueous glycolic acid solution.

e) Reducing Agent Addition Step

The reducing agent addition step is a step of adding a reducing agent to reduce the ferric ions formed from the ferric salt added in the ferric salt addition step to ferrous ions. The timing of performing the reducing agent addition step is not particularly limited as long as the glycolic acid oligomer can be depolymerized in the presence of the ferrous ions in the g) depolymerization step. For example, the e) reducing agent addition step may be performed concurrently with the d) ferric salt addition step, may be performed after the d) ferric salt addition step, or may be performed before the d) ferric salt addition step. In particular, when the e) reducing agent addition step is performed after the ferric salt addition step, the production rate of glycolide tends to be enhanced. Note that the reducing agent step may be performed only once or may be performed twice or more.

As described above, the oxidation-reduction potential from the ferrous ion to the ferric ion is 0.78 V. Therefore, examples of the reducing agent that reduces in the reducing agent addition step include metals, metal compounds, or organic compounds, which have an oxidation-reduction potential of lower than 0.78 V. Specific examples of the reducing agent include copper chloride (CuCl), Mn, and vitamin C. Among these, Mn exhibiting high effect of reduction is preferred.

The addition amount of the reducing agent is not particularly limited as long as the addition amount can reduce the ferric ions originated from the ferric salt and can form adequate amount of ferrous ions. From the perspective of reactivity, the addition amount of the reducing agent is preferably from 0.1 to 20, more preferably from 1 to 10, and even more preferably 2 to 5, when the total amount (mole) of ferric salt added in the d) ferric salt addition step is 1.

Note that the reducing agent may be added directly into the reactor and may be dissolved in, for example, a solvent in advance and then added to the reactor.

2. Glycolide

The glycolide obtained by the production method according to an embodiment of the present invention (also referred to as crude glycolide) is preferably highly pure. Specifically, the purity of the glycolide is preferably 99.0% or greater, more preferably 99.3% or greater, and even more preferably 99.5% or greater. Therefore, according to the method for producing glycolide of an embodiment of the present invention, highly pure glycolide can be obtained at a high production rate.

EXAMPLES

The present invention is described in further detail with reference to examples below. These examples, however, shall not be construed as limiting the scope of the present invention.

Example 1

In a separable flask having a capacity of 1 L, 1.3 kg of 70 mass % aqueous glycolic acid solution (available from Chemours, High Purity grade) was charged, and 0.13 g of ferrous sulfate was added (ferrous salt addition step).

Then, the solution was heated by increasing the temperature from room temperature to 215° C. while being agitated at normal pressure, and polycondensation reaction was performed while formed water was distilled off. Then, the pressure inside the flask was gradually reduced from the normal pressure to 3 kPa, and then heating was performed at 215° C. for 3 hours to distill off low-boiling-point substances, such as unreacted raw materials, and thus a glycolic acid oligomer was obtained (oligomer preparation step).

Then, in a reactor having a capacity of 0.5 L, 120 g of the obtained glycolic acid oligomer, 130 g of tetraethylene glycol dibutyl ether, and 100 g of octyl triethylene glycol were added and then heated to 235° C. to make the reaction system be a homogeneous solution. While this reaction system was heated at a temperature of 235° C. and an agitation speed of 170 rpm, a depolymerization reaction was performed for 12 hours under reduced pressure at 3 kPa. During the reaction, the tetraethylene glycol dibutyl ether and the crude glycolide were co-distilled every 1 hour. The crude glycolide was separated and recovered from the co-distillate, and the mass was measured (depolymerization step). Note that, at the same time as the recovery of the crude glycolide every 1 hour, glycolic acid oligomer in an amount equivalent to the mass of the recovered crude glycolide was charged into the reaction system again. The arithmetic average of the recovered amount per 1 hour of the crude glycolide was calculated and designated as the production rate (distillation rate) of the crude glycolide (g/h).

Example 2

The production rate of crude glycolide was determined in the same manner as in Example 1 except for changing the ferrous salt added in the ferrous salt addition step from the ferrous sulfate to 0.09 g of ferrous chloride.

Comparative Example 1

The production rate of crude glycolide was determined in the same manner as in Example 1 except for changing the ferrous salt addition step to the ferric salt addition step (specifically, changing the ferrous sulfate to 1.63 g of ferric sulfate).

Comparative Example 2

The production rate of crude glycolide was determined in the same manner as in Example 1 except for changing the ferrous salt addition step to the ferric salt addition step (specifically, changing the ferrous sulfate to 0.13 g of ferric chloride).

Example 3

The production rate of crude glycolide was determined in the same manner as in Example 1 except for changing the ferrous salt addition step to the ferric salt addition step and the reducing agent addition step (specifically, changing the ferrous sulfate to 0.10 g of ferric chloride and 0.14 g of copper chloride).

Reference Example 1

The production rate of crude glycolide was determined in the same manner as in Example 1 except for performing no ferrous salt addition step (adding no ferrous sulfate).

Reference Example 2

The production rate of crude glycolide was determined in the same manner as in Example 1 except for performing no ferrous salt addition step (specifically, changing the ferrous sulfate to 0.95 g of copper chloride).

Example 4

In a separable flask having a capacity of 1 L, 1.3 kg of 70 mass % aqueous glycolic acid solution (available from Chemours, High Purity grade) was charged, and 0.13 g of ferric chloride was added (ferric salt addition step).

Then, the solution was heated by increasing the temperature from room temperature to 215° C. while being agitated at normal pressure, and polycondensation reaction was performed while formed water was distilled off. Then, the pressure inside the flask was gradually reduced from the normal pressure to 3 kPa, and then heating was performed at 215° C. for 3 hours to distill off low-boiling-point substances, such as unreacted raw materials, and thus a glycolic acid oligomer was obtained (oligomer preparation step).

Then, in a reactor having a capacity of 0.5 L, 120 g of the obtained glycolic acid oligomer, 130 g of tetraethylene glycol dibutyl ether, and 100 g of triethylene glycol monooctyl ether were added and then heated to 235° C. to make the reaction system be a homogeneous solution. While this reaction system was heated at a temperature of 235° C. and an agitation speed of 170 rpm, a depolymerization reaction was performed for 12 hours under reduced pressure at 3 kPa. During the reaction, the tetraethylene glycol dibutyl ether and the crude glycolide were co-distilled every 1 hour. The crude glycolide was separated and recovered from the co-distillate, and the mass was measured (depolymerization step). Note that, at the same time as the recovery of the crude glycolide every 1 hour, a mixture of metal manganese and glycolic acid oligomer in an amount equivalent to the mass of the recovered crude glycolide was charged into the reaction system again. Note that the amount of the metal manganese to be charged was 1.5-fold mol of the iron ions contained in the glycolic acid oligomer to be charged. Then, the arithmetic average of the recovered amount per 1 hour of the crude glycolide obtained at and after the second time was calculated and designated as the production rate of the crude glycolide (g/h).

Example 5

The depolymerization reaction was performed for 12 hours in the same manner as in Example 1 except for changing the ferrous salt addition step to the ferric salt addition step (specifically, changing the ferrous sulfate to 0.13 g of ferric chloride). After 12 hours had passed, 0.12 g of L(+)-ascorbic acid was added (reducing agent addition step). The depolymerization reaction was then further continued for 1 hour. From the mass of the recovered crude glycolide, the production rate of the crude glycolide (g/h) was determined.

The evaluation results for Examples 1 to 5, Comparative Examples 1 and 2, and Reference Examples 1 and 2 are shown in Table 1.

TABLE 1

| | Iron compound | Reducing agent | Crude glycolide distillation rate (g/h) |
|---|---|---|---|
| Example 1 | $FeSO_4$ | — | 18.9 |
| Example 2 | $FeCl_2$ | — | 18.3 |
| Example 3 | $FeCl_3$ | CuCl | 18.7 |
| Example 4 | $FeCl_3$ | Mn | 17.4 |
| Example 5 | $FeCl_3$ | L(+)-ascorbic acid | 17.8 |
| Comparative Example 1 | $Fe_2(SO_4)_3$ | — | 16.4 |
| Comparative Example 2 | $FeCl_3$ | — | 16.5 |
| Reference Example 1 | — | — | 13.2 |
| Reference Example 2 | — | CuCl | 14.1 |

As shown in Table 1, Examples 1 to 5, in which the depolymerization step was performed in the presence of the ferrous ions, exhibited high distillation rates of crude glycolide, and it is found that all of these exhibited high production rates of glycolide. Furthermore, both the cases where a ferrous salt was added (Examples 1 and 2) and the cases where a ferric salt and a reducing agent were added (Examples 3 to 5) achieved substantially the same results. Furthermore, it was clear that the timing at which the reducing agent was added may be at the same time as the addition of the ferric salt (Example 3) and may be performed concurrently with the depolymerization step (Examples 4 and 5).

On the other hand, the cases where the depolymerization step of the glycolic acid oligomer was performed in the presence of ferric ions (Comparative Examples 1 and 2) exhibited higher production rates of glycolide compared to the cases where no iron compounds were added (Reference Examples 1 and 2), but exhibited lower production rates of glycolide compared to the case where a ferrous salt was added (Examples 1 to 5).

This application claims the priority to JP 2018-052285, filed on Mar. 20, 2018. The content described in this application is hereby incorporated by reference in its entirety.

INDUSTRIAL APPLICABILITY

According to the present invention, a method for producing glycolide, with which a production rate of glycolide can be further enhanced, can be provided.

The invention claimed is:

1. A method for producing glycolide comprising:
   an oligomer preparation step of heating an aqueous glycolic acid solution and subjecting glycolic acid contained in the aqueous glycolic acid solution to dehydrating polycondensation, to obtain a glycolic acid oligomer;
   a depolymerization step of depolymerizing the glycolic acid oligomer in the presence of ferrous ions to obtain glycolide; and
   a ferrous salt addition step of adding a salt of ferrous iron to the aqueous glycolic acid solution,
   wherein an addition amount of the salt of ferrous iron is an amount at which an amount of the ferrous ions obtained from the salt of ferrous iron is from 0.01 to 1000 ppm per weight of the glycolic acid.

2. The method for producing glycolide according to claim 1, wherein, in the depolymerization step, glycolide is recovered by vaporization performed concurrently with the depolymerization reaction.

3. The method for producing glycolide according to claim 2, wherein,
in the depolymerization step, a fresh feed of the glycolic acid oligomer is additionally added.

4. The method for producing glycolide according to claim 1, wherein
the depolymerization step is performed in the presence of a polyalkylene glycol diether represented by Formula (1):

$$X\text{—}O\text{—}(\text{—}R\text{—}O\text{—})_p\text{-}Y \quad (1)$$

where,
R represents a methylene group or a linear or branched alkylene group having from 2 to 8 carbons,
X and Y each independently represent an alkyl group having from 2 to 20 carbons or an aryl group,
p represents an integer of 1 to 5, and
in a case where p is 2 or greater, a plurality of R moieties may be the same or different.

5. The method for producing glycolide according to claim 1, wherein said ferrous salt is ferrous sulfate or ferrous chloride.

6. The method for producing glycolide according claim 1, wherein,
in the depolymerization step, an activator is added to activate deactivated ferrous ions.

* * * * *